United States Patent [19]

Leon

[11] Patent Number: 4,865,813

[45] Date of Patent: Sep. 12, 1989

[54] DISPOSABLE ANALYTICAL DEVICE

[76] Inventor: Luis P. Leon, 109 Buckboard La., Fairfield, Conn. 06430

[21] Appl. No.: 882,167

[22] Filed: Jul. 7, 1986

[51] Int. Cl.$^4$ ............................................. G01N 1/10
[52] U.S. Cl. ..................... 422/101; 422/58;
422/61; 422/68; 422/102; 436/165; 436/178;
436/808; 436/810; 210/198.1; 210/321.84;
210/345; 210/500.21
[58] Field of Search ............. 422/44, 56, 58, 59,
422/61, 68, 101, 102; 436/165, 177, 178, 180,
808, 810; 210/198.1, 500.21, 511, 321.84, 345

[56] References Cited

U.S. PATENT DOCUMENTS

| | | | |
|---|---|---|---|
| 3,849,256 | 11/1974 | Linder | 422/102 X |
| 3,865,548 | 2/1975 | Padawer | 422/61 X |
| 4,042,337 | 8/1977 | Griffith | 422/102 |
| 4,382,000 | 5/1983 | Wisebaker et al. | 422/70 X |
| 4,600,507 | 7/1986 | Shimizu et al. | 422/101 X |
| 4,624,929 | 11/1986 | Ullman | 422/56 X |
| 4,639,316 | 1/1987 | Eldegheidy | 210/433.2 |

FOREIGN PATENT DOCUMENTS

0184852 6/1986 European Pat. Off. ......... 210/433.2

Primary Examiner—Barry S. Richman
Assistant Examiner—Lynn M. Kummert
Attorney, Agent, or Firm—Rodman & Rodman

[57] ABSTRACT

The disposable analytical device includes an outer shell portion having an interior which is divided into reagent chambers and a test sample chamber. The reagent chambers are non-communicable with each other. However the test sample chamber is communicable with each of the reagent chambers through a semi-permeable membrane. The device is formed of an optic quality material to permit analysis of the test results in a spectrophotometer.

26 Claims, 3 Drawing Sheets

DISPOSABLE ANALYTICAL DEVICE

BACKGROUND OF THE INVENTION

This invention relates to test devices for testing the qualities of a test sample, and more particularly, to a disposable test device for performing one or more simultaneous tests on a test sample.

Laboratory tests to determine the characteristics of blood or urine, for example, as a basis for diagnosis or treatment of a patient generally involve a series of tests that are often carried out in sequential fashion.

One known analytical apparatus for performing sequential testing of a test sample is shown in U.S. Pat. No. 3,865,548. The disclosed apparatus includes three chambers separated by at least two semi-permeable membranes. Each chamber is filled with a testing fluid, and analysis of a test sample requires that such sample pass through each test chamber sequentially.

Under this arrangement there is a risk that the integrity of the test sample may be compromised as it progresses to a subsequent test chamber due to possible adulteration in a previous test chamber. Further, since the test chambers are sequentially arranged there are undesirable time delays before all tests are completed as a result of sequential movement of the test sample through the successive test chambers.

U.S. Pat. No. 3,865,548 also shows an embodiment in the form of a syringe for running two tests simultaneously on a test sample disposed in the barrel of the syringe. Two axially directed reagent chambers are provided in a hollow syringe plunger which interact through a membrane with the test sample. Analysis of the reagent chambers using optical methods is difficult to accomplish because of distortion caused by curvature of the hollow plunger. Compensating lenses or special distortion-free flat surfaces must thus be employed on the device. Furthermore, the patented device requires leak-tight moving parts and must therefore be fabricated to high tolerance specifications.

In order to avoid the simultaneous test problems of U.S. Pat. No. 3,865,548, it may be desirable to divide the test sample into sub-samples and place the sub-samples in separate testing devices. However, the division of a test sample and the setting up and use of separate test devices for simultaneous testing of sub-samples is often a cumbersome, expensive and time consuming procedure.

Generally the tests performed on blood or urine samples, for example, are standardized tests, frequently carried out in similar test devices. The labeling provided for such tests normally serves to distinguish one test sample from another. Since hospitals or laboratories will often conduct mass tests of blood or urine samples from different individuals in assembly line fashion, there is a likelihood that labels and/or samples will become mixed up, especially if the samples are divided for separate tests.

It is thus desirable to provide a single analytical test device that can be used for performing a plurality of simultaneous tests on a single test sample and which device does not require special optical corrections, and does not require moving parts. It is also desirable to provide a disposable analytical device for simultaneous testing of a test sample.

OBJECTS AND SUMMARY OF THE INVENTION

Among the several objects of the invention may be noted the provision of a novel disposable analytical device, a novel disposable analytical device that includes at least one chamber having a test sample that communicates with at least one test reagent through a semi-permeable membrane, a novel disposable analytical device having a plurality of analytical reagents disposed in separate chambers, a novel disposable analytical device which is pre-filled with analytical reagents and can be stored prior to use, a novel disposable analytical device wherein the reagent chambers are all communicable with a test sample chamber for simultaneous testing of the test sample, a novel disposable analytical device that is filled one time only with a test sample for one or more separate simultaneous tests and thereafter disposed of when the testing is completed, a novel disposable analytical device which has no moving parts, a novel disposable analytical device which is formed of an optic quality material to permit separate distortion free optical measurements of separate test chambers in the device, and a novel method for analyzing a test sample.

Other objects and features of the invention will be in part apparent and in part pointed out hereinafter.

In accordance with the present invention, the disposable analytical device includes a container having a non-permeable peripheral wall and opposite base portions that define an enclosed interior space. An interior semi-permeable membrane provided in the container extends between the base portions to divide the interior space of the container into at least two communicable chambers.

The semi-permeable membrane is selected such that communication occurs from one of the chambers through the semi-permeable membrane to the other chamber. Thus, if one of the chambers is charged with a test sample to be analyzed, and the other chamber is provided with a predetermined analytical reagent, the test sample can mix with the analytical reagent by movement through the semi-permeable membrane.

The semi-permeable membrane is designed to prevent movement therethrough of enzymes, dyes and other large molecular weight compounds whose size and configuration prevent passage through the semi-permeable membrane. However, smaller molecular weight compounds, such as water, electrolytes and the like can freely cross the semi-permeable membrane. The analytical device is formed of an optic quality material that permits light to pass without distortion through opposite base ends of the analytical reagent chambers, also known as the test chambers, for light measurement purposes.

In one embodiment of the invention, the analytical device includes a plurality of reagent test chambers which are separately communicable with a single test sample chamber to permit simultaneous testing of the test sample. In another embodiment of the invention, the analytical device includes one reagent test chamber and one test sample chamber.

In several embodiments of the invention the plural reagent test chambers surround the test sample chamber in concentric radial arrangement, the number of reagent chambers determining the number of tests that are to be performed on the test sample.

In other embodiments of the invention the reagent test chambers are arranged in a row adjacent the test sample chamber.

When the analytical tests are completed on the test sample, the analytical device can be disposed of.

The invention accordingly comprises the constructions and method hereinafter described, the scope of the invention being indicated in the claims.

DESCRIPTION OF THE DRAWINGS

In the accompanying drawings, in which several embodiments of the invention are illustrated.

FIGS. 5–11 are simplified sectional views of further embodiments of the invention;

FIG. 12 is a simplified perspective view of another embodiment of the invention; and, FIG. 13 is a sectional view thereof.

Corresponding reference characters indicate corresponding parts throughout the several views of the drawings.

DETAILED DESCRIPTION OF THE INVENTION

Figures 1, 2:
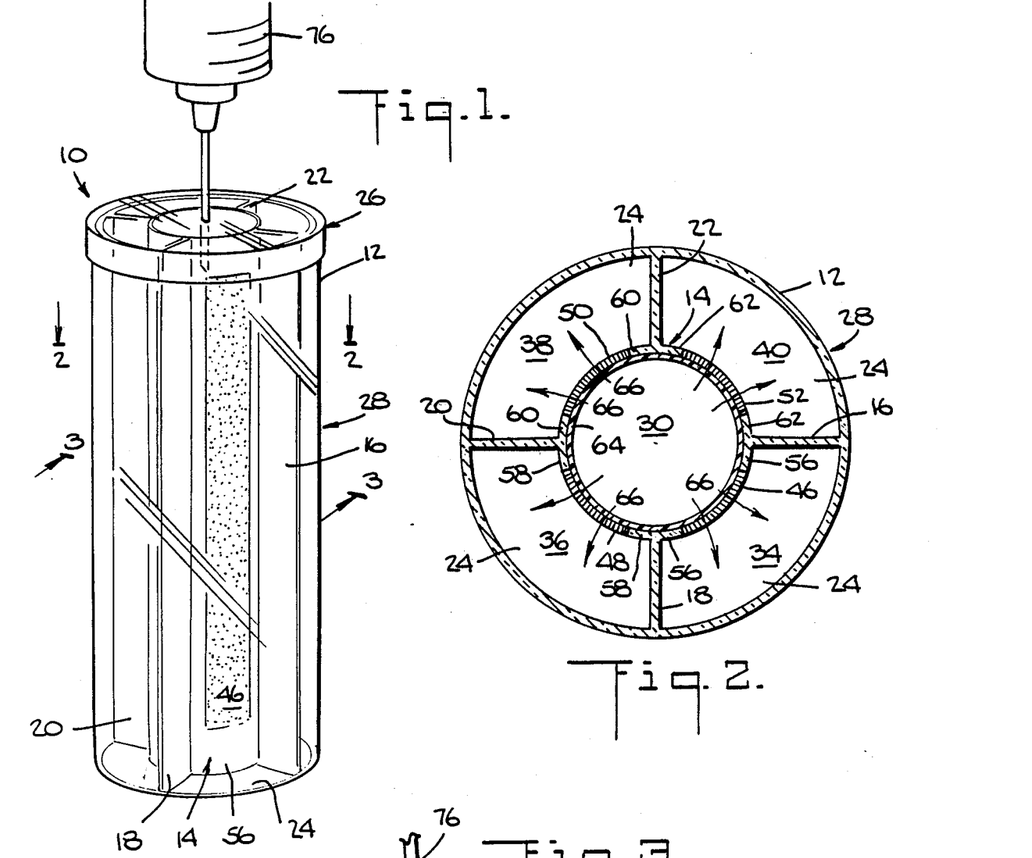
FIG. 1 is a perspective view of a disposable analytical device incorporating one embodiment of the present invention.
FIG. 2 is a sectional view thereof taken on the line 2—2 of FIG. 1.

A disposable analytical device incorporating one embodiment of the invention is generally indicated by the reference number 10 in FIG. 1.

Figure 3:
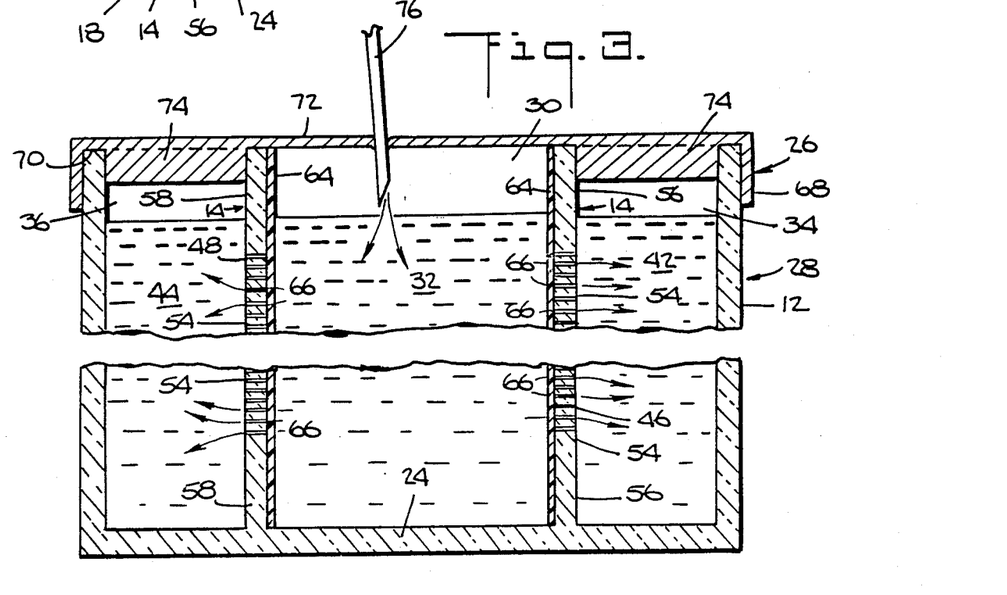
FIG. 3 is an enlarged fragmentary sectional view taken on the line 3—3 of FIG. 1.

Referring to FIGS. 1–3, the device 10 comprises a cylindrical outer shell portion 12. An inner shell portion 14 is joined by radial wall portions 16, 18, 20 and 22 to the outer shell portion 12. The outer shell 12 and the inner shell 14 are closed at one end by a base 24 and open at an opposite end which receives a cover 26.

The inner shell 12, the outer shell 14 and the radial wall portions 16, 18, 20 and 22 are substantially equivalent in height.

Preferably the outer shell 12, the inner shell 14, the radial walls 16, 18, 20 and 22, and the base 24 are integrally molded as a unit, hereinafter referred to as the unit 28. The cover 26 and the unit 28 can be formed of any suitable light transmissible material which does not deleteriously effect the contents of the device 10, such as polystyrene and polypropylene.

A central test chamber 30 is thus defined within the inner shell 14, between the base 24 and the cover 26, and accommodates a test sample 32 (FIG. 3). Referring to FIGS. 2 and 3, a reagent chamber 34 is defined between the outer and inner shells 12 and 14, the radial walls 16 and 18, the base 24 and the cover 26. The outer and inner shells 12, 14, the base 24, and the cover 26 further define similar reagent chambers 36, 38 and 40 between the respective radial wall portions 18–20, 20–22, 22–24. Predetermined test reagents are disposed in the reagent chambers 34, 36, 38 and 40, such as reagent 42 in the reagent chamber 34 (FIG. 3) and reagent 44 in the reagent chamber 36. Preferably the test reagents occupy substantially the entire volume of the reagent chambers 34, 36, 38 and 40.

The outer shell 12, the radial walls 16, 18, 20 and 22, the base 24 and the cover 26 are substantially impermeable to the test sample 32 and the reagents in the reagent chambers 34, 36, 38 and 40. However, predetermined sections of the inner shell 14, such as the sections 46, 48, 50 and 52 (FIG. 2) are rendered porous by a plurality of relatively small openings 54 (FIG. 3). It is these small openings 54 that comprise the semi-permeable membrane 64, which is permeable to low molecular weight metabolites present in the test sample 32, but impermeable to larger molecular weight compounds, such as enzymes and dyes.

As most clearly shown in FIG. 1, a non-permeable border portion 56 of the inner shell 14, surrounds the porous section 46 in the reagent chamber 34. Similar non-porous sections 58, 60 and 62 (FIG. 2) surround the respective porous sections 48, 50 and 52 in the reagent chambers 36, 38 and 40.

The semi-permeable sleeve-like membrane 64 is heat-sealed, bonded or otherwise secured in leak-tight fashion to the inner shell 14 within the test sample chamber 30. The semi-permeable membrane 64 can be classified as hydrophilic or hydrophobic. The hydrophilic semi-permeable membrane 64, can be formed of a suitable material such as cellophane, cuprophane, cellulose acetate, polyethylene, polypropylene or nylon. Silicon is exemplary of a hydrophobic semi-permeable membrane. The semi-permeable membrane 64 is secured to the inner shell 14 at the non-permeable border portions 56, 58, 60 and 62.

Silicon membranes can be used for analyzing gases such as $CO_2$ in the human blood, and under specified conditions, can also be used to analyze hydrophobic-like metabolics such as tryglycerides and cholesterol.

The semi-permeable membranes can be designed to be even more specifically restrictive to relatively smaller molecules than enzymes or dyes, such as NADH (nicotinamide adenine dinucleotide), ATP (adenosine triphosphate), and the like.

Under this arrangement the test sample 32 is communicable with the reagent chambers 34, 36, 38 and 40 through the semi-permeable membrane 64. The enzymes, dyes and other large molecular weight components in the reagents 42 and 44 contained in the reagent chambers 34 and 36, respectively, as well as the enzymes, dyes and other large molecular weight components in the reagents (not shown) in reagent chambers 38 and 40 are not communicable with the test sample 32 across the semi-permeable membrane 64.

The general direction of communication between the test sample 32 and the reagent chambers 34, 36, 38 and 40 is in the directions shown by the arrows 66 in FIGS. 2 and 3. It should also be noted that the area of the respective porous sections 56, 58, 60 and 62 need not be identical, as for example for the purpose of establishing different flow rates from the test sample chamber 30 to the reagent chambers 34, 36, 38 and 40.

The cover 26, as most clearly shown in FIG. 3, includes a peripheral flange 68 which collars the outer shell 12. An annular groove 70 in the cover 26 at the flange 68 is formed to accommodate the outer shell 12. A reduced central section 72 of the cover 26 aligns with the test sample chamber 30. Under this arrangement a non-reduced annular section 74 of the cove 26 essentially plugs the reagent chambers 34, 36, 38 and 40, thus assuring the isolation of the test sample chamber 30 from the reagent chambers 34, 36, 38 and 40. Although not shown, radial grooves which correspond to the radial wall portions 16, 18, 20 and 22 are formed in the non-reduced annular section 74 to receive the radial wall portions 16, 18, 20 and 22.

In using the analytical test device 10, the reagent chambers 34, 36, 38 and 40 are filled with test reagent to a predetermined capacity before the cover 26 is placed in position. The central test chamber 30 is generally filled with a sample diluent reagent. Chamber 30 can also contain a reagent, such as an enzyme, for producing a chemical reaction. In certain situations, chamber 30 can be left empty, to be subsequently charged with a test sample when appropriate The cover 26 can be bonded or otherwise irremovably joined to the unit 28 once the reagent chambers are filled.

Reagents are selected for the reagent chambers 34, 36, 38 and 40 based upon the type of tests for which the device 10 will be used. The device 10 can thus be used as a standardized test device for testing of blood and urine samples, or other test samples which generally require a series of analytical tests.

When the test sample 32 is to be tested in the device 10, a hypodermic needle 76 is used to collect the test sample 32 and dispense such sample into the central test chamber 30 through the reduced central section 72 of the cover 26.

It should be noted that the irremovable placement of the cover 26 on the unit 28 after the reagent chambers 34, 36, 38 and 40 are filled is intended to preserve the integrity of the reagents previously disposed in the reagent chambers 30, 34, 36, 38 and 40. These reagents can include unique stabilized enzyme formulations. The enzymes can be free in solution or immobilized at the interior surface of the shell 12 and/or the semi-permeable membrane 64. The charging of the test sample chamber 30 with the test sample 32 through the reduced central section 72 also avoids the possibility of contaminating the reagents already disposed in the reagent chambers 34, 36, 38 and 40.

Once the test sample 32 is charged in the central test chamber 30, there is a migration of the test sample 32 through the semi-permeable membrane 64 and the porous sections 46, 48, 50 and 52 of the respective reagent chambers 34, 36, 38 and 40.

After a predetermined migration period, the reagent chambers of the device 10 can be analyzed in a suitable known optical instrument such as a optical spectrophotometer, for optical analysis of the reagent test chambers 34, 36, 38 and 40.

Figure 4:
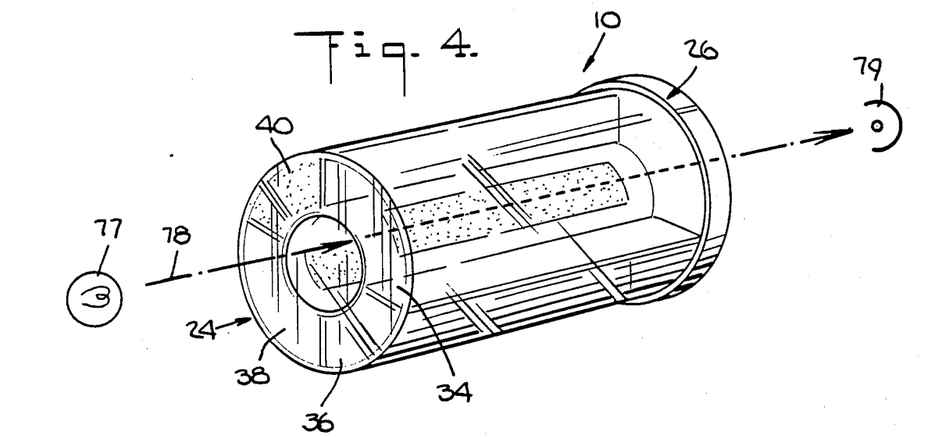
FIG. 4 is a simplified perspective view thereof showing the manner in which light rays pass through the device for optical measurement purposes.

For example, as shown in FIG. 4, a light source 77 in the spectrophotometer (not shown) will transmit light rays 78 through the reagent chambers 36, 38, 40 and 42 to a receiver 79 for measurement and analysis.

It is a relatively simple matter to perform an optical analysis of the device 10 since light rays can be directed through the base 24 and the cover 26, which are generally flat surfaces. The flat surface of the base 24 and the cover 26 permits distortion free passage of the light rays 78 into the base 24, through the reagent chambers 36, 38, 40 and 42, and out of the cover 26 to the receiver 79.

Other optical analytical instruments can also be used depending on the test requirements, including a colorimeter, a fluorometer and a nephelometer.

Some of the tests which can be performed with the device 10 include a determination of:

Glucose
Uric Acid
Urea Nitrogen
Calcium
Sodium
Potassium
Cholesterol
Triglycerides
Alanine Aminotransferase
Aspartate Aminotransferase
Lactate Dehydrogenase
Alkaline Phosphotase
Glutamyltransferase
Acid Phosphotase
Enzyme Immuno Assay Reactions One of the advantages of the analytical device is that in the case of whole blood, centrifugation to separate red blood cells is unnecessary since the red blood cells will not pass through the semi-permeable membrane 64.

Another advantage of the analytical device presents itself in tests involving serum containing high concentrations of substances such as bilirubin, lipimia, and hemolysis turbidity, which are known to interfere in clinical tests. These interfering substances will not pass through the membrane, and thereby will be eliminated from the test analysis.

In carrying out some of these tests, the following reagents would be provided in the reagent chambers 34, 36, 38 and 40.

| Test Sample: Whole blood or human serum. | | |
|---|---|---|
| Reagent Chamber | Test | Reagent |
| 30 | — | buffer, catalase |
| 34 | Glucose | buffer, glucose oxidase, 4-aminoantipyrine, dihydroxybenzene sulfonic acid, peroxidase |
| 36 | Urea Nitrogen | buffer, urease, malic dehydrogenase, NADH, ketoglutaric acid |
| 38 | Uric Acid | buffer, uricase, 4-aminoantipyrine, dihydroxybenzene sulfonic acid, peroxidase |
| 40 | Creatinine | buffer, creatine amidinohydrolase, creatinine amidohydrolase, sarcosine oxidase, peroxidase, 4-aminoantipyrine, dihydroxybenzene sulfonic acid |

In the Glucose, Urea Nitrogen, Uric Acid and Creatinine reactions, the primary events taking place in the analytical device are:

1. Dialyzable metabolites from the test sample 32 such as glucose, urea nitrogen, uric acid and creatinine, indiscriminately diffuse across the semi-permeable membrane 66 into the reagent chambers 34, 36, 38 and 40.

2. In each reagent chamber 34, 36, 38 and 40, specific reactions are triggered by the specific enzymes contained in that chamber. Due to the large molecular size and structural configuration, the enzymes cannot diffuse across the semi-permeable membrane 66 and therefore, are restricted to a specific chamber. For example, in the reagent chamber 34, for the glucose test, the enzyme glucose oxidase is present and this enzyme breaks down only glucose to produce hydrogen peroxide ($H_2O_2$) as one of its byproducts. Similarly, the enzymes urease (chamber 36), uricase (chamber 38) and creatinine amidohydrolase (chamber 40) will break down urea nitrogen, uric acid and creatinine, respectively. Except for urea nitrogen, one of the reaction products is hydrogen peroxide. Urea by the action of urease will produce ammonia.

3. In the reagent chamber 34 where $H_2O_2$ is a byproduct, the enzyme peroxidase catalyzes the coupling of 4-aminoantipyrine with dihydroxybenzene sulfonic acid to form the indamine dye. This dye is of relatively large molecular weight and cannot diffuse across the semi-permeable membrane. The dye color intensity is then measured in a suitable spectrophotometer and it is directly proportional to the concentration of the metabolite present in the test sample 32.

In the case of urea (urease reaction) the coupling reaction oxidizes NADH to NAD. NAD is then quantitated at 340 nanometers (nm) in a suitable spectrophotometer and it is directly proportional to the urea present in the test sample 32.

The typical reactions involved in the reagent chambers 34, 36, 38 and 40 include:

1. Glucose: (Reagent Chamber 34)

(a) Glucose + $O_2$  $H_2O_2$
(sample)

(b) $H_2O_2$ + 4AA + DHBS  indamine dye
(500 nm)

2. Urea Nitrogen: (Reagent Chamber 36)

(a) BUN  $NH_3^+$

(b) NADH + $NH_3$ + α-KG  NAD

3. Uric Acid: (Reagent Chamber 38)

(a) Uric acid  $H_2O_2$
(sample)

(b) $H_2O_2$ + 4AA + DHBS  indamine dye
(500 nm)

4. Creatinine: (Reagent Chamber 40)

(a) Creatinine + $O_2$  Creatine (b) Creatine + $O_2$  Sarcosine (c) Sarcosine  $H_2O_2$ (d) $H_2O_2$ + 4AA + DHBS  indamine dye
(500 nm)

After the reagent chambers 36, 38, 40 and 42 have been subject to an optical analysis, the device 10 can be disposed of.

The precise dimensions of the analytical device 10 may vary depending upon the nature of the test sample 32, the type of test or tests that are to be carried out upon the test sample 32, and the type of optical analytical instruments being used.

Nevertheless, to exemplify the magnitudes being dealt with, the overall height of the device 10 can be approximately 4 to 5 centimeters. The diameter of the inner shell 14 can be approximately 1 centimeter and the diameter of the outer shell 12 can be approximately 1.5 to 2 centimeters. The thickness of the outer and inner shells 12 and 14 and the base 24 can be approximately 1 to 1.5 millimeters. The thickness of the semi-permeable membrane 64 can be in the range of 0.1 to 1.5 mils. The reduced central section 72 of the cover 26 can be approximately 1 to 2 mils and the non-reduced annular section can be approximately 1 to 2 millimeters thick.

It will be apparent that since the disposable device 10 includes four reagent chambers, four separate tests can be performed on the test sample 32 in simultaneous fashion.

Figure 5:
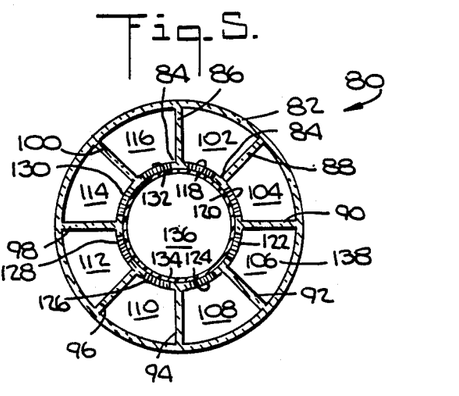

Another embodiment of the disposable analytical device is generally indicated by the reference number 80 in FIG. 5. The disposable device 80 includes an outer shell 82 and an inner shell 84 joined by radial wall portions 86, 88, 90, 92, 94, 96, 98 and 100 which define reagent chambers 102, 104, 106, 108, 110, 112, 114 and 116.

The inner shell 84 includes porous sections 118, 120, 122, 124, 126, 128, 130 and 132 in the respective reagent chambers 102–116. A semi-permeable sleeve-like membrane 134 identical to the semi-permeable membrane 64 is heat-seal bonded or otherwise secured in leak-tight fashion to the inner shell 84 within a central test sample chamber 136 defined by the inner shell 84. The bonding is accomplished in a manner similar to that previously described for the device 10.

Thus, the semi-permeable membrane 134 is bonded to the inner shell 84 at non-permeable border portions of the shell that surround the porous sections 118–132.

A suitable cover member (not shown) incorporating the design characteristics of the cover member 26 covers one end of the disposable device 80, the other end thereof being sealed by a base 138 similar to the base 24. Preferably the shells 80, 82, the radial wall portions 86–100 and the base 138 are molded as a unit.

The device 80 is used in a manner similar to that described for the device 10. However since the device 80 includes eight reagent test chambers, it has the potential of performing eight simultaneous tests on a single test sample disposed within the test sample chamber 136. Optical analysis of the eight reagent chambers of the device 80 is also accomplished in distortion free fashion in a manner similar to that shown in FIG. 4.

Figures 6, 7, 8:
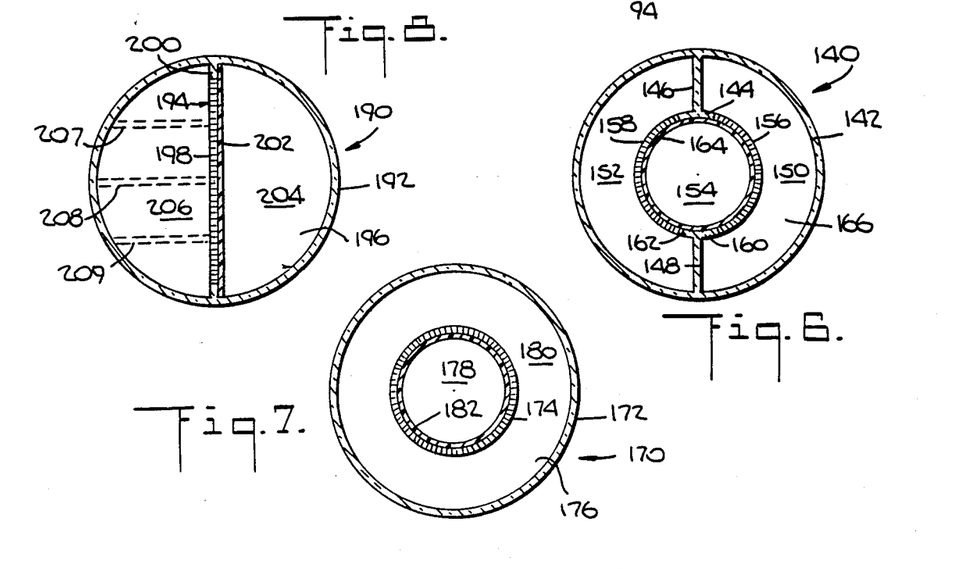

A further embodiment of the disposable analytical device is generally indicated by the reference number 140 in FIG. 6.

The disposable analytical device 140 includes an outer shell 142 and an inner shell 144 joined by radial wall portions 146 and 148. Under this arrangement there are two reagent chambers 150, 152 and a central test chamber 154. The reagent chambers 150 and 152 include respective porous sections 156 and 158 surrounded by respective non-permeable border portions 160 and 162.

A semi-permeable membrane 164 identical to the membrane 64 is heat seal bonded or otherwise secured in leak-tight fashion to the inner shell 144 within the test chamber 154 at the non-permeable border portions 160 and 162. The device 140 includes a base 166 and an appropriate cover member (not shown) that employs the design principles of the cover member 26. Preferably the shells 142, 144, the radial walls 146, 148 and the base 166 are molded as a unit.

The device 140 is used in a manner similar to that previously described for the device 10. However the device 140 which includes two reagent chambers, performs two tests in simultaneous fashion on a single test sample disposed in the test chamber 154.

Still another embodiment of the disposable analytical device is generally indicated by the reference number 170 in FIG. 7. The device 170 includes an outer shell 172, an inner shell 174 and a base 176 preferably formed as a unit.

Under this arrangement a central test chamber 178 is surrounded by a reagent test chamber 180. The inner shell 174 can be provided with alternate porous and non-permeable sections to facilitate securance of a semipermeable membrane 182 identical to the membrane 64.

An appropriate cover member (not shown) employing the design principles of the cover 26 is installed on the device 170. The device 170 is used in a manner similar to that previously described for the device 10. However, since the device 170 includes one reagent chamber 180, a single test is performed on the test sample disposed in the test chamber 178.

Another embodiment of the disposable analytical device is generally indicated by the reference number 190 in FIG. 8. The device 190 comprises a generally cylindrical shell portion 192 divided in substantially equal halves by a partition 194. Preferably the shell portion 192, the partition 194 and a base 196 are molded as a unit. The partition 194 can include one or more porous sections 198 and a non-porous border portion 200 for securance of a semi-permeable membrane 202.

Under this arrangement the device 190 includes a test chamber 204 and a reagent chamber 206 of substantially equal volume. An appropriate cover member (not shown) incorporating the design characteristics of the cover 26 is installed on the device 190. If desired the reduced section of the cover member (not shown) can be of smaller area than the cross section of the test chamber 204. It should be noted that the primary purpose of the reduced section is to permit charging of the test chamber 204 and such purpose can be accomplished within a relatively small area.

The device 190 is used in a manner similar to that previously described for the device 10.

It should be noted that the device 190 can be provided with two or more reagent chambers by dividing the existing reagent chamber 206. This division is accomplished by including division walls 207, 208, 209 shown dotted in the chamber 206. The division walls 207, 208 and 209 are non-permeable and the reagent chambers formed by such division walls include corresponding non-porous border portions (not shown) on the partition wall 194 for securance of the semi-permeable membrane. The modified device 190 thus provides four reagent test chambers with two different volumes for performing four tests in a manner similar to that previously described for the device 10.

Figure 9:
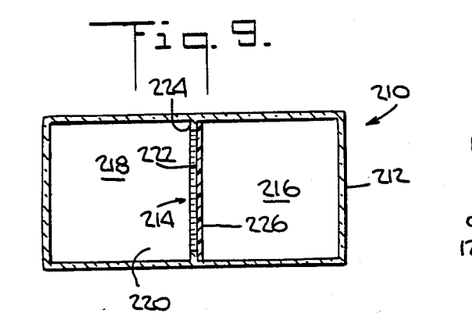

Still another embodiment of the disposable analytical device is generally indicated by the reference number 210 in FIG. 9. The device 210 comprises a generally rectangular shell portion 212 divided by a partition wall 214 into two chambers 216 and 218 of substantially equal volume.

Preferably the rectangular shell 212, the partition wall 214 and a base 220 are integrally molded as a unit. The partition wall 214 is formed with a porous section 222 and a non-porous border portion 224. A semipermeable membrane 226 is heat-seal bonded or otherwise secured in leak-tight fashion to the partition wall 214 within the chamber 218. Thus the chamber 218 constitutes the test chamber and the chamber 216 constitutes the reagent chamber.

An appropriate cover member (not shown) incorporating the design principles of the cover 26, covers the device 210. A portion of the cover member includes a reduced section to facilitate charging of the test chamber 218. The device 210 is used in a manner similar to that previously described for the device 10.

Figures 10, 11, 12, 13:
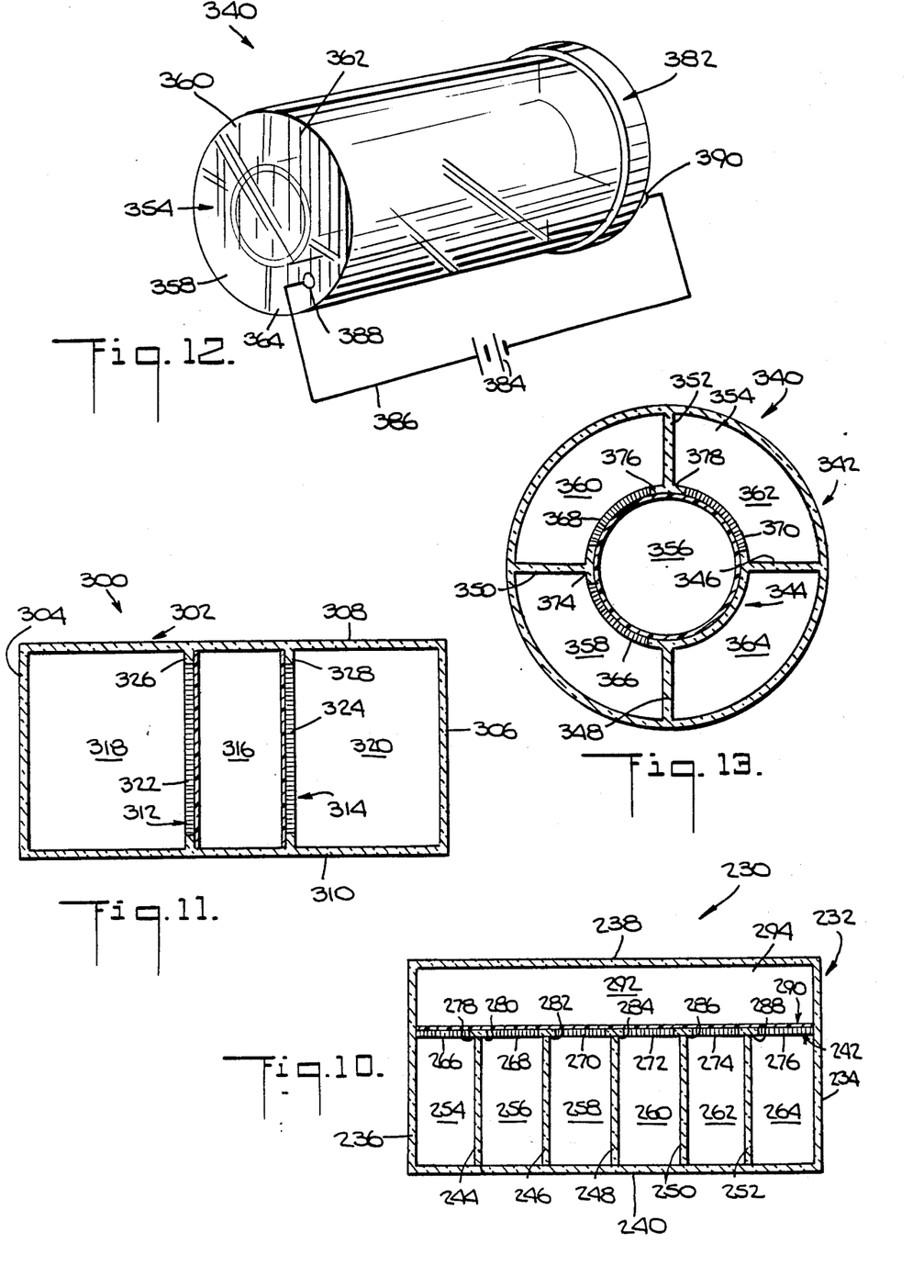

A further embodiment of the invention is generally indicated by the reference number 230 in FIG. 10. The device 230 comprises a generally rectangular shell portion 232 having two opposite short sides 234, 236 and two opposite long sides 238, 240. An elongated partition wall 242 extends across the shell 232 from the side 234 to the side 236.

A series of section walls 244, 246, 248, 250 and 252, extend from the partition wall 242 to the long wall 240 to define reagent chambers 254, 256, 258, 260, 262 and 264.

The partition wall 242 includes predetermined porous sections 266, 268, 270, 272, 274 and 276 respectively surrounded by non-porous border portions 278, 280, 282, 284, 286 and 288. A semi-permeable membrane 290 is secured in leak-tight fashion to the partition wall 242 at the non-porous border portions 278-288.

An unsectioned test chamber 292 is defined between the partition wall 242 and the long wall 238. A suitable cover member (not shown) incorporating the design principles of the cover member 26, covers one end of the shell 232, the other end having a base 294 molded integrally with the shell 232. Since the device 260 has six reagent chambers, six separate tests can be conducted simultaneously in a manner similar to that previously described for the device 10.

Another embodiment of the invention is generally indicated by the reference number 300 in FIG. 11. The device 300 comprises a generally rectangular shell portion 302 having two opposite short sides 304, 306 and two opposite long sides 308, 310. A pair of spaced partition walls 312 and 314 extend from the long side 308 to the long side 310 to define a test chamber 316 therebetween.

A reagent chamber 318 is defined between the partition wall 312 and the short wall 304, whereas a reagent chamber 320 is defined between the partition wall 314 and the short wall 306. The partition walls 312, 314 respectively include porous sections 322, 324 surrounded by non-porous border portions 326, 328. Semipermeable membranes 330 and 332 ar secured to the respective partition walls 312, 314 at the non-porous border portions 326, 328 of the reagent chambers 318, 320.

A suitable cover member (not shown) incorporating the design characteristics of the cover member 26, covers one end of the shell 302, the other end having a base 334 integrally molded with the shell 302. Since the device 300 has two reagent chambers, two separate tests can be conducted simultaneously in a manner similar to that previously described for the device 10.

A further embodiment of the invention is generally indicated by the reference number 340 in FIG. 12. Referring to FIG. 13, the device 340 comprises an outer shell 342, an inner shell 344 joined by radial wall portions 346, 348, 350 and 352, and a base 354. Under this arrangement, a central test chamber 356 is surrounded by three reagent chambers 358, 360, 362 and a reference chamber 364.

The inner shell 344 includes porous sections 366, 368 and 370 at the respective reagent chambers 358, 360 and 362 surrounded by non-porous border portions 374, 376 and 378. However, the inner shell 344 is non porous at the reference chamber 364.

A semi-permeable membrane 380 identical to the membrane 64 is secured in leak-tight fashion to the inner shell 344 within the test chamber 356 at the non-porous border portions 374, 376, 378 and at predetermined areas that confront the reference chamber 364. Under this arrangement there is no communication across the inner shell 344 between the test chamber 356 and the reference chamber 364. The device 340 also includes a cover member 382 identical to the cover member 26 opposite the base end 354.

Prior to using the device 340, a selected buffered reagent is charged in the reagent chambers 358, 360 and 362, and a suitable electrolyte salt such as saturated potassium chloride is charged in the reference chamber 364. In using the device 340, a test sample such as human whole blood or serum is charged into the test chamber 356 through the cover 372 in the manner described for the device 10.

A predetermined voltage such as supplied by a battery 384 is applied across the reference chamber 364 by, for example, employing a conductor 386 connected at 388 to the base 344 and connected at 390 to the cover 372. Electrolytes such as $Na^+$, $K^+$ and $Cl^-$ diffuse across the semi-permeable membrane into chambers 358, 360 and 362. Each of these chambers is equipped with ion specific electrodes. Quantitation of the electrolytes is carried out by reading the rate of change of potential or current, by means of, for example, a differential amplifier.

As will be apparent to those skilled in the art, the semi-permeable membranes can be bonded directly to the radial wall portions and/or shells of the various embodiments and thus eliminate the inner shells and partitions which serve primarily to support the semi-permeable membranes.

In the case of the device 170 which has no radial walls, the semi-permeable membrane 182 can be provided as a free-standing structure.

In the device 190, the semi-permeable membrane can be secured directly to the interior surface of the shell 192 to eliminate the partition 194.

In the devices 210, 230 and 300, the semi-permeable membranes can likewise be bonded to the inner surface of the shell and the section walls thereby eliminating the partition walls.

In the foregoing arrangements where the inner shell or partition walls are omitted, the semi-permeable membrane may be provided with added thickness at the bonding sites.

It will also be apparent that the cover members of each embodiment constitute a base end of the device.

Some advantages of the present invention evident from the foregoing description include a disposable analytical device which permits simultaneous testing of a single test sample with a plurality of test reagents. The number of tests which can be accomplished simultaneously is based upon the number of reagent chambers provided in the device.

It will be apparent from the various embodiments of the invention that any selected plural number of reagent chambers and any selected reagent chamber capacity can be provided in the disposable analytical device. Furthermore, the reagent chambers can be prefilled and sealed at the manufacturing stage of the device. Thus, the devices can be stocked in quantity for use on an as-needed basis without any initial preparation other than the charging of the test sample into the device. A further advantage is that once a test or series of tests have been completed the disposable analytical device can be discarded.

All embodiments of this invention permit easy base-end-to-cover-end distortion free optical analysis of the reagent test chambers. Since the analytical device has no moving parts, operation thereof is relatively simple.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An article of manufacture in the form of a disposable analytical device for testing the properties of a test sample comprising:
   (a) a container having opposite base portions and a non-permeable imperforate outer peripheral portion extending between said opposite base portions to define an enclosed interior space,
   (b) a semi-permeable membrane within said outer peripheral portion extending from one said base portion to the other said base portion for dividing said interior space into separate chambers having corresponding opposite closed base ends corresponding to said opposite base portions,
   (c) a test sample to be analyzed being chargeable in one of said chambers through one of said base portions, the opposite base portions being imperforate,
   (d) the other of said chambers being sealed at said opposite base ends by said opposite base portions and including nonpermeable baffle means to subdivide the other said chamber into at least two non-communicable reagent chambers each said reagent chamber having a predetermined analytical reagent contained therein, said non-permeable baffle means extending away from said semi-permeable membrane to said outer peripheral portion to permit common communication between said one of said chambers and the respective said at least two reagent chambers,
   (e) said semi-permeable membrane and said analytical reagents being selected such that communication occurs from said one of said chambers through said semi-permeable membrane to each of said at least two reagent chambers,
   (f) said container having no inlet nor outlet flow means such that any fluid disposed within said one of said chambers and said at least two reagent chambers remains inside said container, and
   (g) said base portions being light transmitting for permitting light to pass through said at least two reagent chambers in predetermined fashion for light measurement purposes.

2. The device as claimed in claim 1 wherein said semi-permeable membrane joins the opposite base portions in leak-tight arrangement.

3. The device as claimed in claim 1 wherein one of said base portions comprises a cover member through which said one chamber is charged with said test sample.

4. The device as claimed in claim 1 wherein said one of said base portions comprises a cover member, said outer peripheral portion and said other base portion together constituting a component of said device that is attachable to said shell portion to form said one base portion of said device.

5. The device as claimed in claim 1 wherein said semi-permeable membrane is supported by a perforated support member.

6. The device as claimed in claim 1 wherein said container is of a first predetermined size and shape and has a first closed periphery and a first cross-section, said semi-permeable membrane being of a second predetermined size and shape and having a second closed periphery and a second cross-section, said semi-permeable membrane being disposed in said container such that said second closed periphery is spaced radially inwardly from said first closed periphery.

7. The device as claimed in claim 6 including a space within said second closed periphery and wherein the space within said second closed periphery defines one of said chambers and the space between said first and second closed peripheries defines the other of said chambers.

8. The device as claimed in claim 6 wherein said container and said semi-permeable membrane are generally circular in cross section.

9. The device as claimed in claim 1 wherein said baffle means comprises a baffle member having opposite end portions joined to the respective opposite base portions of said container.

10. The device as claimed in claim 9 wherein said baffle means comprises a predetermined plurality of said baffle members spaced from each other to define a corresponding predetermined plurality of said reagent chambers.

11. The device as claimed in claim 10 wherein said container and said semi-permeable membrane are generally circular in cross section and said baffle members extend radially away from said semi-permeable membrane to said non-permeable outer peripheral portion.

12. The device of claim 11 wherein one of said reagent chambers is a reference chamber for electrical testing and includes electrical terminals at opposite base portions of said container, a non-permeable wall being provided between said reference chamber and said test sample chamber.

13. The device as claimed in claim 11 wherein said non-permeable outer peripheral portion and said baffle member are integrally joined.

14. The device as claimed in claim 10 including four baffle members in said other of said chambers to divide said other of said chambers into four non-communicable reagent chambers.

15. The device as claimed in claim 10 including eight baffle members in said other of said chambers to divide said other of said chambers into eight non-communicable reagent chambers.

16. The device as claimed in claim 10 including five baffle members in said other of said chambers to divide said other of said chambers into six non-communicable reagent chambers.

17. The device as claimed in claim 1 wherein said container is of a first predetermined size and shape and has a first closed periphery, said semi-permeable membrane being of a second predetermined size and shape and extending across the first closed periphery of said container.

18. The device as claimed in claim 17 wherein said semi-permeable membrane extends across said first closed periphery to divide the enclosed interior space into a space on one side of said semi-permeable membrane that defines said one chamber and a space on the other side of said semi-permeable membrane defines said other chamber.

19. The device as claimed in claim 17 wherein non-permeable baffle means are provided in said other chamber to subdivide the other of said chambers into at least two reagent chambers.

20. An article of manufacture in the form of a disposable analytical device for testing the properties of a test sample comprising,
   (a) a container having an imperforate non-permeable outer peripheral wall, a base and a cover member to define an enclosed interior space,
   (b) a semi-permeable membrane extending from said base to said cover member to divide said interior space into two separate chambers having corresponding opposite closed base ends corresponding to said base and said cover member, respectively,
   (c) a test sample to be analyzed being disposable in one of said chambers,
   (d) the other of said chambers being sealed at said opposite ends by said base and said cover member, respectively and including nonpermeable baffle means to subdivide the other said chamber into at least two noncommunicable reagent chambers, each said reagent chamber having a predetermined analytical reagent container therein, said nonpermeable baffle means extending away from said semipermeable membrane to said outer peripheral wall to permit common communication between said one of said chambers and the respective said at least two reagent chambers,
   (e) said semi-permeable membrane and said analytical reagents being selected such that communication occurs from said one of said chambers through said semi-permeable membrane to each of said at least two reagent chambers, and
   (f) said base and said cover member being light transmitting for permitting light to pass through said at least two reagent chambers in predetermined fashion for light measurement purposes.

21. An article of manufacture in the form of a disposable analytical device for testing the properties of a test sample comprising,
   (a) a container having opposite base portions and a non-permeable imperforate outer peripheral portion extending between said opposite base portions to define an enclosed interior space,
   (b) a pair of spaced apart semi-permeable membranes within said outer peripheral portion extending from one said base portion to the other said base portion and between opposite sides of said outer peripheral portion for dividing said interior space into three separate chambers having corresponding opposite closed base ends corresponding to said opposite base portions,
   (c) a test sample to be analyzed being chargeable in one of said three chambers defined in part by said pair of semi-permeable membranes, through one of said base portions, the opposite base portion being imperforate,
   (d) the other two of said three chambers being reagent chambers sealed at said opposite base ends by said opposite base portions and each of said reagent chambers having a predetermined analytical reagent contained therein, (e) said semi-permeable membranes and said analytical reagents selected such that communication occurs from said one chamber through the respective said semi-permeable membranes to the respective said two reagent chambers, (f) said container having no inlet nor outlet flow means such that any fluid disposed within said one chamber and said two reagent chambers remains inside said container, and (g) said base portions being light transmitting for permitting light to pass through said two reagent chambers in predetermined fashion for light measurement purposes.

22. An article of manufacture in the form of a disposable analytical device for testing the properties of a test sample comprising, (a) a container having an imperforate non-permeable outer peripheral wall, a base and a cover member to define an enclosed interior space, (b) a pair of spaced apart semi-permeable membranes extending from said base to said cover member and between opposite sides of said outer peripheral wall to divide said interior space into three separate chambers wherein two of said chambers are spaced from each other by the third said chamber, said third chamber being defined in part by the spaced-apart semi-permeable membranes, said two of said chambers are non-communicable with each other but are each communicable with said third chamber via said semi-permeable membranes, said three chambers having corresponding opposite closed base ends corresponding to said base and said cover member, respectively, (c) a test sample to be analyzed being disposable in said third chamber, (d) said two of said chambers being reagent chambers sealed at said opposite base ends by said base and said cover member, respectively, and each of said reagent chambers having a predetermined analytical reagent contained therein, (e) said semi-permeable membrane and said analytical reagents being selected such that communication occurs from said third chamber through the respective said semi-permeable membranes to the respective said two reagent chambers, and (f) said base and said cover member being light transmitting for permitting light to pass through said two reagent chambers in predetermined fashion for light measurement purposes.

23. The device as claimed in claim 21 wherein said semi-permeable membrane joins the opposite base portions in leak-tight arrangement.

24. The device as claimed in claim 21 wherein one of said base portions comprises a cover member through which said one chamber is charged with said test sample.

25. The device as claimed in claim 21 wherein said one of said base portions comprises a cover member, said outer peripheral portion and said other base portion together constituting a shell portion, said cover member being a positionable component of said device that is attachable to said shell portion to form said one base portion of said device.

26. The device as claimed in claim 21 wherein said semi-permeable membranes are supported by a perforated support member.

* * * * *